United States Patent
Cai et al.

(10) Patent No.: US 10,017,473 B1
(45) Date of Patent: Jul. 10, 2018

(54) METHOD FOR PREPARING PENTACHLOROPYRIDINE BY UTILIZING DCTF RECTIFYING SHORT STEAMING RESIDUES

(71) Applicant: YANCHENG INSTITUTE OF TECHNOLOGY, Yancheng (CN)

(72) Inventors: Zhaosheng Cai, Yancheng (CN); Denghao Min, Yancheng (CN); Cheng Ding, Yancheng (CN); Xuemei Zhu, Yancheng (CN); Huaihong Zhang, Yancheng (CN)

( * ) Notice: Subject to any disclaimer, the term of this patent is extended or adjusted under 35 U.S.C. 154(b) by 0 days.

(21) Appl. No.: 15/405,292

(22) Filed: Jan. 12, 2017

(51) Int. Cl.
*C07D 213/04* (2006.01)
*C07D 213/26* (2006.01)

(52) U.S. Cl.
CPC .................................. *C07D 213/04* (2013.01)

(58) Field of Classification Search
CPC .............................. C07D 213/04; C07D 213/26
See application file for complete search history.

(56) References Cited

FOREIGN PATENT DOCUMENTS

| CN | 105037256 | * | 11/2015 | ........... C07D 213/61 |
|---|---|---|---|---|
| CN | 105061298 | * | 11/2015 | ........... C07D 213/61 |

* cited by examiner

*Primary Examiner* — Noble E Jarrell
(74) *Attorney, Agent, or Firm* — Wayne & Ken, LLC; Tony Hom

(57) ABSTRACT

A method for preparing pentachloropyridine by utilizing DCTF rectifying short steaming residues, comprising the following steps: converting polymers in the residues through in situ catalytic cracking and vacuum distillation by using the catalytic degradation function of a catalyst formed by aluminum oxide, silicon oxide, zirconia, 4A zeolite, magnesium oxide, mordenite and HZSM-5 zeolite on the polymers in the DCTF rectifying short steaming residues into small molecular compounds and obtaining pentachloropyridine-containing crude oil; washing the pentachloropyridine-containing crude oil by using an aqueous solution of an alkaline assistant formed by sodium carbonate, potassium carbonate, sodium bicarbonate, potassium bicarbonate, ammonium bicarbonate and sodium hydroxide, carrying out reduced pressure rectification, refrigerating crystallization, vacuum filtration or centrifuging separation, solvent washing, and vacuum drying method sequentially to obtain a pentachloropyridine product with a mass percentage content greater than 95% at a yield being 1-15% of the mass of the DCTF rectifying short steaming residues.

6 Claims, 3 Drawing Sheets

METHOD FOR PREPARING PENTACHLOROPYRIDINE BY UTILIZING DCTF RECTIFYING SHORT STEAMING RESIDUES

TECHNICAL FIELD

The present invention relates to a method for preparing pentachloropyridine by utilizing DCTF rectifying short steaming residues, which is a new method for realizing efficient utilization of recycling of chemical byproducts in preparation of fine organic chemicals in fine organic synthesis field.

BACKGROUND OF THE PRESENT INVENTION

DCTF, chemical name 2,3-dichloro-5-(trifluoromethyl) pyridine, CAS No. 69045-84-7, is a colorless and transparent liquid with relative density of 1.55 (water is 1.0) under room temperature. As an important pesticide and medicine intermediate, DCTF can not only be used for production of fluoric herbicide such as fluazifop-butyl, haloxyfop-ethoxyethyl and haloxyfop, but also be widely applied in production of fluorine-containing benzoylurea pesticides such as fluazuron and chlorfluazuron, insecticides such as high efficiency fungicide fluazinam and fluorine-containing medicines. These agricultural chemicals take DCTF as one of raw materials, which has characteristics of high efficacy and low toxicity, and distinctive characteristics of low pollution and environmentally friendly, so DCTF is developed rapidly in more than a decade.

Preparation of DCTF mainly includes following methods: (1) taking 2-amino-5-methylpyridine as raw material, generating 2-amino-3-chloro-5-(trichloromethyl) pyridine by chlorination, obtaining 2,3-dichloro-5-(trichloromethyl) pyridine by diazotization and replacing diazo group by hydrogen in the presence of the catalyst such as $Cu_2Cl_2$, and obtaining DCTF by the reaction of 2,3-dichloro-5-(trichloromethyl) pyridine and hydrogen fluoride in the presence of the catalyst such as mercuric oxide or mercuric fluoride; (2) taking 2-chloro-5-methylpyridine as raw material, carrying out side chain chlorination under photocatalysis to obtain 2-chloro-5-(trichloromethyl) pyridine, carrying out ring chlorination to obtain 2,3-dichloro-5-(trichloromethyl) pyridine catalyzed by the catalyst such as lewis acid, and obtaining DCTF by the reaction of 2,3-dichloro-5-(trichloromethyl) pyridine and hydrogen fluoride in the presence of the catalyst such as mercuric oxide or mercuric fluoride; (3) taking 3-methylpyridine as raw material, generating 3-(trichloromethyl) pyridine by the reaction with chlorine under photocatalysis, carrying out ring chlorination to obtain 2,3-dichloro-5-(trichloromethyl) pyridine catalyzed by the catalyst lewis acid, and obtaining DCTF by the reaction of 2,3-dichloro-5-(trichloromethyl) pyridine and hydrogen fluoride in the presence of the catalyst such as mercuric oxide or mercuric fluoride; (4) taking 2-chloro-5-chloromethyl pyridine as raw material, carrying out photochlorination to generate 2-chloro-5-(trichloromethyl) pyridine, generating 2,3-dichloro-5-(trichloromethyl)pyridine by heat-chlorination catalyzed by the catalyst such as lewis acid, and obtaining DCTF by the reaction of 2,3-dichloro-5-(trichloromethyl) pyridine and hydrogen fluoride in the presence of the catalyst such as mercuric oxide or mercuric fluoride. Among these methods, the process for producing DCTF by taking 2-chloro-5-chloromethyl pyridine as raw material is more widely applied in production of DCTF due to various advantages such as low raw material cost, high reaction selectivity and good product quality.

In the process for producing DCTF by taking 2-chloro-5-chloromethyl pyridine, 3-methylpyridine or 2-chloro-5-methylpyridine as raw material, the reaction material is obtained by the reaction of 2,3-dichloro-5-(trichloromethyl) pyridine and hydrogen fluoride in the presence of the catalyst such as mercuric oxide or mercuric fluoride, the reaction material should be primarily short steamed to generate short steaming liquid containing DCTF, and DCTF product is obtained by further rectifying the obtained short steaming liquid. However, in this process, DCTF rectifying short steaming residues will be produced. Most of the substances in these rectifying short steaming residues are substituted pyridine compound containing multiple halogen atoms and their polymers in molecular structure, however, they are difficult to be harmless treated by simple incineration method due to no combustibility or low combustibility. So how to treat DCTF rectifying short steaming residues efficiently, realize separation and purification or conversion of contained substances, reduce production cost of DCTF and potential pollution and hazardous of DCTF rectifying short steaming residues on environment, and increase effective utilization of resources sufficiently have become an important task of concerns gradually in recent years.

SUMMARY OF PRESENT INVENTION

A method for preparing pentachloropyridine by utilizing DCTF rectifying short steaming residues of the invention is to carry out efficiently treatment on the produced DCTF short steaming residues in primary steaming before rectifying separation on the reaction material containing DCTF after fluoridation in the process for producing 2,3-dichloro-5-(trichloromethyl) pyridine by photo-chlorination, heat chlorination and fluoridation and prepare pesticide and medicine intermediate pentachloropyridine by taking DCTF rectifying short steaming residues as one of basic raw materials, thereby increasing effective utilization of resources, reduce production cost of DCTF and potential pollution and hazardous of DCTF rectifying short steaming residues on environment.

The technical scheme of the invention is as follows: adding a catalyst and DCTF rectifying short steaming residues respectively into a reactor according to a mass ratio of 0.01~20:0.01~90 by using the differences in volatility, solubleness and boiling point between polymers formed by chloropyridine compound, chlorofluoropyridine compound and fluoropyridine compound under high temperature in the DCTF rectifying short steaming residues and chloropyridine compound, fluoropyridine compound, and chlorofluoropyridine compound as well as catalytic degradation function of a catalyst formed by aluminum oxide, silicon oxide, zirconia, 4A zeolite, magnesium oxide, mordenite and HZSM-5 zeolite according to a mass ratio of 0.01~50:0.01~60:0.001~10:0.01~80:0.001~10:0.01~30:10.01~10 on the polymers, stirring and converting polymers formed by chloropyridine compound, chlorofluoropyridine compound and fluoropyridine compound under high temperature in the DCTF rectifying short steaming residues through in situ catalytic cracking and vacuum distillation under a condition of 0.001 MPa~0.101 MPa vacuum degree and 100~400DEG C. into chloropyridine small molecular compound and fluoropyridine small molecular compound containing pentachloropyridine, 2,5,6-trichloro-3-(trifluoromethyl) pyridine, 2,3-dichloro-5-(trichloromethyl) pyridine, 2,3,4,6-tetrachloro-5-(trifluoromethyl) pyridine, 2,3,6-trichloro-5-

(dichlorofluoromethyl) pyridine, 2,3,6-trichloro-5-(difluorochloromethyl) pyridine, 5,6-dichloro-3-(hydroxymethyl) pyridine-2-phenol, 2,3-dichloro-5-(dichlorofluoromethyl) pyridine, and 2,3-dichloro-5-(difluorochloromethyl) pyridine, separating with polymers difficult to crack formed in rectifying short steaming process with reaction material containing DCTF, and obtaining crude oil containing pentachloropyridine;

washing the pentachloropyridine-containing crude oil by using an aqueous solution of 0.1% of mass fraction of an alkaline assistant formed by sodium carbonate, potassium carbonate, sodium bicarbonate, potassium bicarbonate, ammonium bicarbonate and sodium hydroxide according to a mass ratio of 0.01~10:0.01~8:0.01~10:0.01~5:0.001~8:0.001~10 to remove acidic material contained in the pentachloropyridine-containing crude oil, carrying out reduced pressure rectification on the alkaline washed pentachloropyridine-containing crude oil, collecting 90~110 DEG C./100~1000 Pa fraction, conducting refrigerating crystallization, vacuum filtration or centrifuging separation to realize separation of pentachloropyridine with other chloropyridine compounds and fluorochloropyridine compounds in the crude oil and obtaining pentachloropyridine crude product; washing the obtained pentachloropyridine crude product after vacuum filtration or centrifuging separation with a mixed solvent formed by petroleum ether, diethyl ether isooctane, benzene, methylbenzene and dimethylbenzene according to a mass ratio of 0.01~100:0.001~20:0.001~100:0.01~50:0.001~8:0.001~10:0.001~10, drying the obtained solid pentachloropyridine product under a condition of 0.001 MPa~0.101 MPa vacuum degree and 10~50 DEG C., and obtaining pentachloropyridine product with a mass percentage content greater than 95% at a yield being 1~15% of the mass of the DCTF rectifying short steaming residues.

DETAILED DESCRIPTION OF PREFERRED EMBODIMENTS

Figure 1:
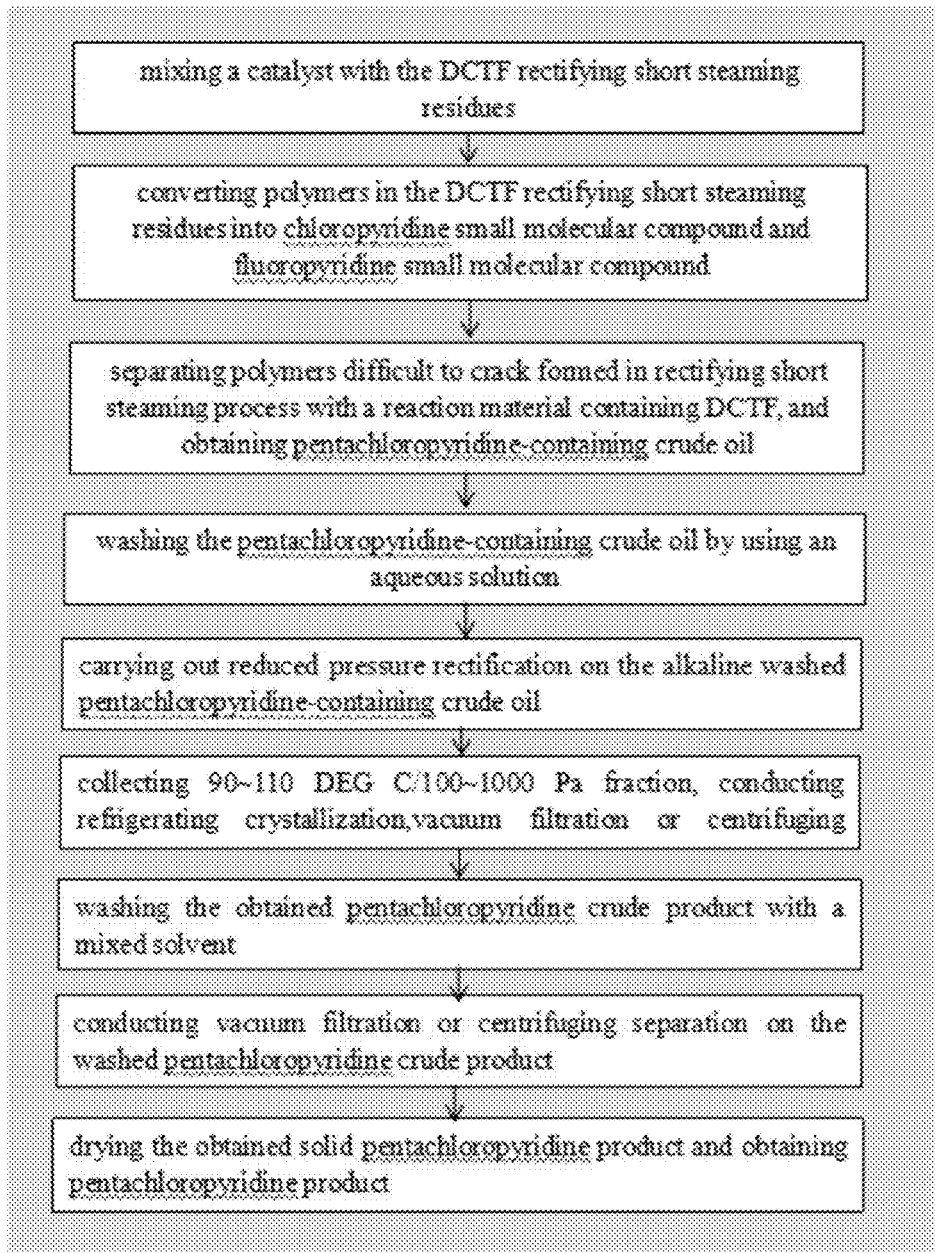
FIG. 1 is a flow diagram of the method for preparing pentachloropyridine by utilizing DCTF rectifying short steaming residues.
Figure 2:
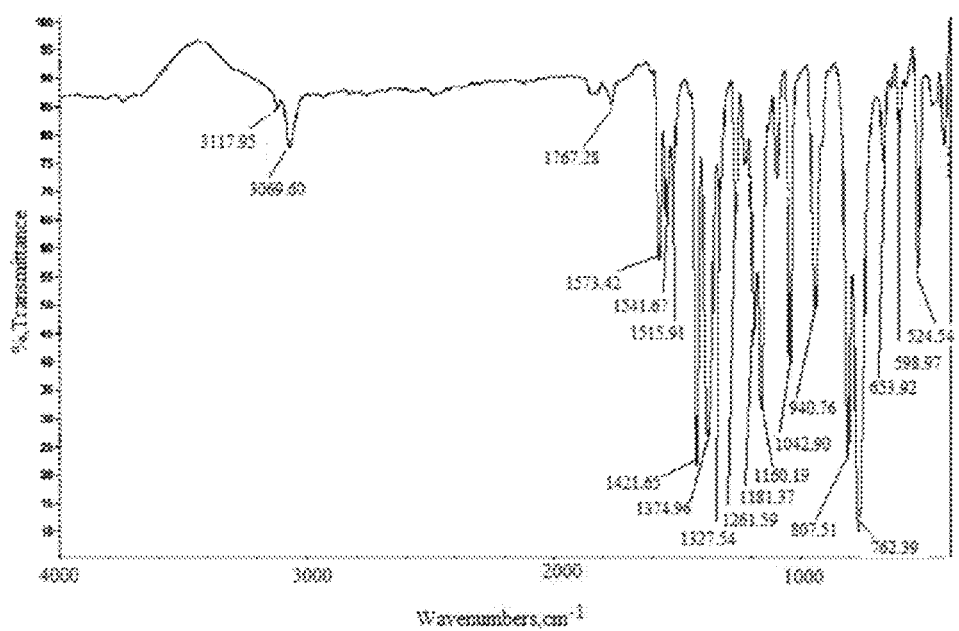
FIG. 2 is Fourier Transform infrared spectroscopy (FT-IR) diagram of pentachloropyridine.
Figure 3:
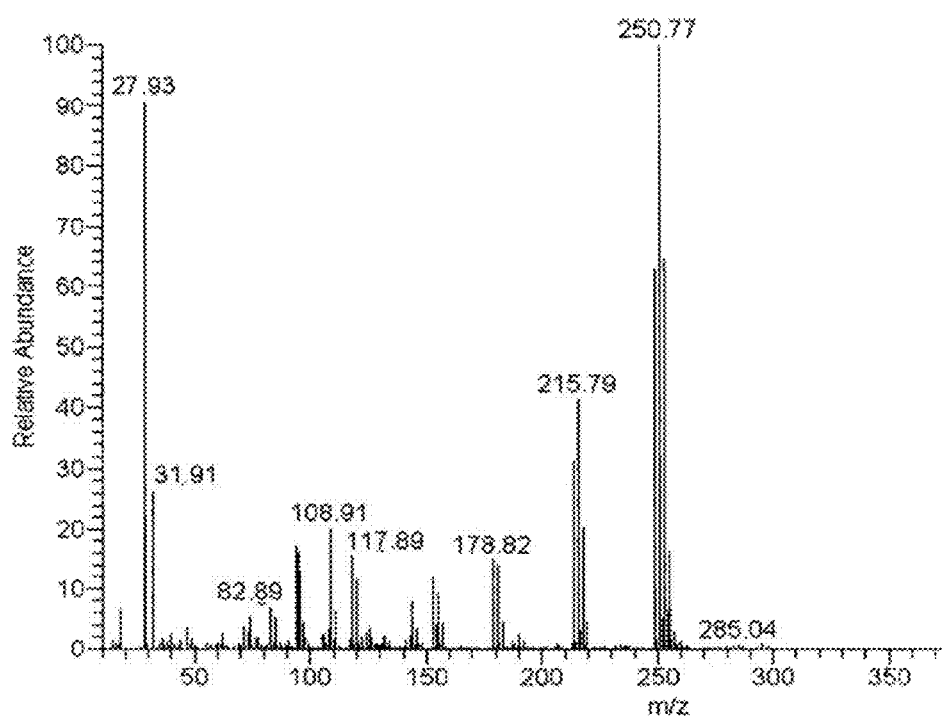
FIG. 3 is Mass Spectrum (MS) diagram of pentachloropyridine.

The invention is further explained in conjunction with the following embodiments.

Embodiment 1

Adding 1000 g DCTF rectifying short steaming residues and 100 g catalyst formed by aluminum oxide, silicon oxide, zirconia, 4A zeolite, magnesium oxide, mordenite and HZSM-5 zeolite according to a mass ratio of 0.01:30:10:20:10:0.01:0.1 into a reactor, stirring and realizing in situ catalytic cracking and vacuum distillation of DCTF rectifying short steaming residues under a condition of 0.01 MPa vacuum degree and 400DEG C. Converting polymers formed by chloropyridine compound, chlorofluoropyridine compound and fluoropyridine compound under high temperature in the DCTF rectifying short steaming residues into chloropyridine small molecular compound and fluoropyridine small molecular compound containing pentachloropyridine, 2,5,6-trichloro-3-(trifluoromethyl) pyridine, 2,3-dichloro-5-(trichloromethyl) pyridine, 2,3,4,6-tetrachloro-5-(trifluoromethyl) pyridine, 2,3,6-trichloro-5-(dichlorofluoromethyl) pyridine, 2,3,6-trichloro-5-(difluorochloromethyl) pyridine, 5,6-dichloro-3-(hydroxymethyl) pyridine-2-phenol, 2,3-dichloro-5-(dichlorofluoromethyl) pyridine, and 2,3-dichloro-5-(difluorochloromethyl) pyridine, separating with polymers difficult to crack formed in rectifying short steaming process with reaction material containing DCTF, and obtaining crude oil containing pentachloropyridine, washing the pentachloropyridine-containing crude oil by using an aqueous solution of 0.1% of mass fraction of an alkaline assistant formed by sodium carbonate, potassium carbonate, sodium bicarbonate, potassium bicarbonate, ammonium bicarbonate and sodium hydroxide according to a mass ratio of 0.1:8:0.01:0.5:4:5 to remove acidic material contained in the pentachloropyridine-containing crude oil, carrying out reduced pressure rectification on the alkaline washed pentachloropyridine-containing crude oil, collecting 90~110 DEC C/100~1000 Pa fraction, conducting refrigerating crystallization, vacuum filtration or centrifuging separation to realize separation of pentachloropyridine with other chloropyridine compounds and fluorochloropyridine compounds in the crude oil and obtaining a pentachloropyridine crude product; washing the obtained pentachloropyridine crude product after vacuum filtration or centrifuging separation with a mixed solvent formed by petroleum ether, diethyl ether isooctane, benzene, methylbenzene and dimethylbenzene according to a mass ratio of 0.01:20:0.1:15:0.001:1:3.1, drying the obtained solid pentachloropyridine product under a condition of 0.08 Mpa vacuum degree and 30DEG C., and obtaining a pentachloropyridine product with a mass percentage content being 96% at a yield being 10% of the mass of the DCTF rectifying short steaming residues.

Embodiment 2

Adding 1000 g DCTF rectifying short steaming residues and 50 g catalyst formed by aluminum oxide, silicon oxide, zirconia, 4A zeolite, magnesium oxide, mordenite and HZSM-5 zeolite according to a mass ratio of 0.1:2:1:0.1:3:0.1:0.01 into the reactor, stirring and realizing in situ catalytic cracking and vacuum distillation of DCTF rectifying short steaming residues under a condition of 0.05 MPa vacuum degree and 350 DEG C. Converting polymers formed by chloropyridine compound, chlorofluoropyridine compound and fluoropyridine compound under high temperature in the DCTF rectifying short steaming residues into chloropyridine small molecular compound and fluoropyridine small molecular compound containing pentachloropyridine, 2,5,6-trichloro-3-(trifluoromethyl) pyridine, 2,3-dichloro-5-(trichloromethyl)pyridine, 2,3,4,6-tetrachloro-5-(trifluoromethyl) pyridine, 2,3,6-trichloro-5-(dichlorofluoromethyl) pyridine, 2,3,6-trichloro-5-(difluorochloromethyl) pyridine, 5,6-dichloro-3-(hydroxymethyl) pyridine-2-phenol, 2,3-dichloro-5-(dichlorofluoromethyl) pyridine, and 2,3-dichloro-5-(difluorochloromethyl) pyridine, separating with polymers difficult to crack formed in rectifying short steaming process with reaction material containing DCTF, and obtaining crude oil containing pentachloropyridine; washing the pentachloropyridine-containing crude oil by using an aqueous solution of 1% of mass fraction of an alkaline assistant formed by sodium carbonate, potassium carbonate, sodium bicarbonate, potassium bicarbonate, ammonium bicarbonate and sodium hydroxide according to a mass ratio of 1:0.8:0.1:5:0.4:0.5 to remove acidic material contained in the pentachloropyridine-containing crude oil, carrying out reduced pressure rectification on the alkaline washed pentachloropyridine-containing crude oil, collecting 90~110 DEG C./100~1000 Pa fraction, conducting refrigerating crystallization, vacuum filtration or centrifuging separation to realize separation of pentachloropyridine with other chloropyridine compounds and fluorochloropyridine compounds in the crude oil and obtaining a pentachloropyridine crude product, washing the obtained pentachloropyridine crude product after vacuum filtration or centrifuging separation with a mixed solvent formed by petroleum ether, diethyl ether isooctane, benzene, methylbenzene and dimethylbenzene according to a mass ratio of 100:10:0.1:3:8:10:10, drying the obtained solid pentachloropyridine product under a condition of 0.10 Mpa vacuum degree and 30DEG C., and obtainings pentachloropyridine product with a mass percentage content being 98.7% at a yield being 1% of the mass of the DCTF rectifying short steaming residues.

Embodiment 3

Adding 1000 g DCTF rectifying short steaming residues and 10 g catalyst formed by aluminum oxide, silicon oxide, zirconia, 4A zeolite, magnesium oxide, mordenite and HZSM-5 zeolite according to a mass ratio of 1:0.2:1:0.01:15:10:10 into the reactor, stirring and realizing in situ catalytic cracking and vacuum distillation of DCTF rectifying short steaming residues under a condition of 0.09 MPa vacuum degree and 300 DEG C. Converting polymers formed by chloropyridine compound, chlorofluoropyridine compound and fluoropyridine compound under high temperature in the DCTF rectifying short steaming residues into chloropyridine small molecular compound and fluoropyridine small molecular compound containing pentachloropyridine, 2,5,6-trichloro-3-(trifluoromethyl) pyridine, 2,3-dichloro-5-(trichloromethyl) pyridine, 2,3,4,6-tetrachloro-5-(rifluoromethyl) pyridine, 2,3,6-trichloro-5-(dichlorofluoromethyl) pyridine, 2,3,6-trichloro-5-(difluorochloromethyl) pyridine, 5,6-dichloro-3-(hydroxymethyl) pyridine-2-phenol, 2,3-dichloro-5-(dichlorofluoromethyl) pyridine, and 2,3-dichloro-5-(difluorochloromethyl) pyridine, separating with polymers difficult to crack formed in rectifying short steaming process with reaction material containing DCTF, and obtaining crude oil containing pentachloropyridine; washing the pentachloropyridine-containing crude oil by using an aqueous solution of 5% of mass fraction of an alkaline assistant formed by sodium carbonate, potassium carbonate, sodium bicarbonate, potassium bicarbonate, ammonium bicarbonate and sodium hydroxide according to a mass ratio of 10:0.01:10:5:4:10 to remove acidic material contained in the pentachloropyridine-containing crude oil, carrying out reduced pressure rectification on the alkaline washed pentachloropyridine-containing crude oil, collecting 90~110 DEG C./100~1000 Pa fraction, conducting refrigerating crystallization, vacuum filtration or centrifuging separation to realize separation of pentachloropyridine with other chloropyridine compounds and fluorochloropyridine compounds in the crude oil and obtaining a pentachloropyridine crude product; washing the obtained pentachloropyridine crude product after vacuum filtration or centrifuging separation with a mixed solvent formed by petroleum ether, diethyl ether isooctane, benzene, methylbenzene and dimethylbenzene according to a mass ratio of 100:0.02:30:50:4:0.5:10, drying the obtained solid pentachloropyridine product under a condition of 0.09 Mpa vacuum degree and 20DEG C., and obtaining a pentachloropyridine product with a mass percentage content being 98% at a yield being 5% of the mass of the DCTF rectifying short steaming residues.

Embodiment 4

Adding 1000 g DCTF rectifying short steaming residues and 5 g catalyst formed by aluminum oxide, silicon oxide, zirconia, 4A zeolite, magnesium oxide, mordenite and HZSM-5 zeolite according to a mass ratio of 30:60:0.01:40:3:15:10 into the reactor, stirring and realizing in situ catalytic cracking and vacuum distillation of DCTF rectifying short steaming residues under a condition of 0.09 MPa vacuum degree and 300 DEG C. Converting polymers formed by chloropyridine compound, chlorofluoropyridine compound and fluoropyridine compound under high temperature in the DCTF rectifying short steaming residues into chloropyridine small molecular compound and fluoropyridine small molecular compound containing pentachloropyridine, 2,5,6-trichloro-3-(trifluoromethyl) pyridine, 2,3-dichloro-5-(trichloromethyl) pyridine, 2,3,4,6-tetrachloro-5-(rifluoromethyl) pyridine, 2,3,6-trichloro-5-(dichlorofluoromethyl) pyridine, 2,3,6-trichloro-5-(difluorochloromethyl) pyridine, 5,6-dichloro-3-(hydroxymethyl) pyridine-2-phenol, 2,3-dichloro-5-(dichlorofluoromethyl) pyridine, and 2,3-dichloro-5-(difluorochloromethyl) pyridine, separating with polymers difficult to crack formed in rectifying short steaming process with reaction material containing DCTF, and obtaining crude oil containing pentachloropyridine; washing the pentachloropyridine-containing crude oil by using an aqueous solution of 10% of mass fraction of an alkaline assistant formed by sodium carbonate, potassium carbonate, sodium bicarbonate, potassium bicarbonate, ammonium bicarbonate and sodium hydroxide according to a mass ratio of 10:4:5:5:3:10 to remove acidic material contained in the pentachloropyridine-containing crude oil, carrying out reduced pressure rectification on the alkaline washed pentachloropyridine-containing crude oil, collecting 90~110 DEG C./100~1000 Pa fraction, conducting refrigerating crystallization, vacuum filtration or centrifuging separation to realize separation of pentachloropyridine with other chloropyridine compounds and fluorochloropyridine compounds in the crude oil and obtaining a pentachloropyridine crude product; washing the obtained pentachloropyridine crude product after vacuum filtration or centrifuging separation with a mixed solvent formed by petroleum ether, diethyl ether isooctane, benzene, methylbenzene and dimethylbenzene according to a mass ratio of 100:0.02:0.01:50:4:0.01:5, drying the obtained solid pentachloropyridine product under a condition of 0.09 Mpa vacuum degree and 20DEG C., and obtaining a pentachloropyridine product with a mass percentage content being 98.5% at a yield being 3% of the mass of the DCTF rectifying short steaming residues.

Embodiment 5

Adding 1000 g DCTF rectifying short steaming residues and 3 g catalyst formed by aluminum oxide, silicon oxide, zirconia, 4A zeolite, magnesium oxide, mordenite and HZSM-5 zeolite according to a mass ratio of 50:30:0.1:37:5:18:9 into the reactor, stirring and realizing in situ catalytic cracking and vacuum distillation of DCTF rectifying short steaming residues under a condition of 0.098 MPa vacuum degree and 260 DEC C. Converting polymers formed by chloropyridine compound, chlorofluoropyridine compound and fluoropyridine compound under high temperature in the DCTF rectifying short steaming residues into chloropyridine small molecular compound and fluoropyridine small molecular compound containing pentachloropyridine, 2,5,6-trichloro-3-(trifluoromethyl) pyridine, 2,3-dichloro-5-(trichloromethyl) pyridine, 2,3,4,6-tetrachloro-5-(trifluoromethyl) pyridine, 2,3,6-trichloro-5-(dichlorofluoromethyl) pyridine, 2,3,6-trichloro-5-(difluorochloromethyl) pyridine, 5,6-dichloro-3-(hydroxymethyl) pyridine-2-phenol, 2,3-dichloro-5-(dichlorofluoromethyl) pyridine, and 2,3-dichloro-5-(difluorochloromethyl) pyridine, separating with polymers difficult to crack formed in rectifying short steaming process with reaction material containing DCTF, and obtaining crude oil containing pentachloropyridine; washing the pentachloropyridine-containing crude oil by using an aqueous solution of 15% of mass fraction of an alkaline assistant formed by sodium carbonate, potassium carbonate, sodium bicarbonate, potassium bicarbonate, ammonium bicarbonate and sodium hydroxide according to a mass ratio of 9:8:7:5:8:10 to remove acidic material contained in the pentachloropyridine-containing crude oil, carrying out reduced pressure rectification on the alkaline washed pentachloropyridine-containing crude oil, collecting 90~110 DEG C./100~1000 Pa fraction, conducting refrigerating crystallization, vacuum filtration or centrifuging separation to realize separation of pentachloropyridine with other chloropyridine compounds and fluorochloropyridine compounds in the crude oil and obtaining pentachloropyridine crude product; washing the obtained pentachloropyridine crude product after vacuum filtration or centrifuging separation with the mixed solvent formed by petroleum ether, diethyl ether isooctane, benzene, methylbenzene and dimethylbenzene according to a mass ratio of 100:0.02:0.01:50:4:0.01:5, drying the obtained solid pentachloropyridine crude product under a condition of 0.09 Mpa vacuum degree and 20DEG C., and obtaining pentachloropyridine product with the mass percentage content being 98.5% at a yield being 3% of the mass of the DCTF rectifying short steaming residues.

We claim:

1. A method for preparing pentachloropyridine by utilizing DCTF rectifying short steaming residues, characterized in that the method comprises the following steps:

mixing a catalyst formed by aluminum oxide, silicon oxide, zirconia, 4A zeolite, magnesium oxide, mordenite and HZSM-5 zeoliteon with the DCTF rectifying short steaming residues;

converting polymers formed by chloropyridine compound, chlorofluoropyridine compound and fluoropyridine compound under high temperature in the DCTF rectifying short steaming residues into chloropyridine small molecular compound and fluoropyridine small molecular compound containing pentachloropyridine, 2,5,6-trichloro-3-(trifluoromethyl) pyridine, 2,3-dichloro-5-(trichloromethyl) pyridine, 2,3,4,6-tetrachloro-5-(trifluoromethyl) pyridine, 2,3,6-trichloro-5-(dichlorofluoromethyl)pyridine, 2,3,6-trichloro-5-(difluorochloromethyl) pyridine, 5,6-dichloro-3-(hydroxymethyl)pyridine-2-phenol, 2,3-dichloro-5-(dichlorofluoromethyl)pyridine, and 2,3-dichloro-5-(difluorochloromethyl) pyridine through in situ catalytic cracking and vacuum distillation under a condition of 0.001 MPa~0.101 MPa vacuum degree and 100~400 DEG C.;

separating polymers difficult to crack formed in rectifying short steaming process with a reaction material containing DCTF, and obtaining pentachloropyridine-containing crude oil;

washing the pentachloropyridine-containing crude oil by using an aqueous solution of 0.01~20% of mass fraction of an alkaline assistant formed by sodium carbonate, potassium carbonate, sodium bicarbonate, potassium bicarbonate, ammonium bicarbonate and sodium hydroxide to remove acidic material contained in the pentachloropyridine-containing crude oil;

carrying out reduced pressure rectification on the alkaline washed pentachloropyridine-containing crude oil sequentially, collecting 90~110 DEG C./100~1000 Pa fraction, conducting refrigerating crystallization, vacuum filtration or centrifuging separation to realize separation of pentachloropyridine with other chloropyridine compounds and fluorochloropyridine compounds in the crude oil and obtaining pentachloropyridine crude product;

washing the obtained pentachloropyridine crude product with a mixed solvent formed by petroleum ether, diethyl ether isooctane, benzene, methylbenzene and dimethylbenzene; and conducting vacuum filtration or centrifuging separation on the washed pentachloropyridine crude product to obtain a solid pentachloropyridine product, and drying the obtained solid pentachloropyridine product under a condition of 0.001 Mpa~0.101 Mpa vacuum degree and 20DEG C., and obtaining pentachloropyridine product with a mass percentage content greater than 95%.

2. The method for preparing pentachloropyridine by utilizing DCTF rectifying short steaming residues according to claim 1, characterized in that a mass ratio of the catalyst formed by aluminum oxide, silicon oxide, zirconia, 4A zeolite, magnesium oxide, mordenite and HZSM-5 zeolite is 0.01~50:0.01~60:0.001-10:0.01~80:0.001~10:0.01~30:0.01~10.

3. The method for preparing pentachloropyridine by utilizing DCTF rectifying short steaming residues according to claim 1, characterized in that a mass ratio between the catalyst and DCTF rectifying short steaming residues is 0.01~20:0.01~90.

4. The method for preparing pentachloropyridine by utilizing DCTF rectifying short steaming residues according to claim 1, characterized in that a mass ratio of the alkaline assistant formed by sodium carbonate, potassium carbonate, sodium bicarbonate, potassium bicarbonate, ammonium bicarbonate and sodium hydroxide is 0.01~10:0.01~8:0.01~10:0.01~5:0.001~8:0.001~10.

5. The method for preparing pentachloropyridine by utilizing DCTF rectifying short steaming residues according to claim 1, characterized in that a mass ratio of the mixed solvent formed by petroleum ether, diethyl ether isooctane, benzene, methylbenzene and dimethylbenzene is 0.01~100:0.001~20:0.001~100:0.01~50:0.001~8:0.001~10:0.001~10.

6. The method for preparing pentachloropyridine by utilizing DCTF rectifying short steaming residues according to claim 1, characterized in that the pentachloropyridine product is obtained at a yield being 1-15% of the mass of the DCTF rectifying short steaming residues.

* * * * *